United States Patent [19]

Mulder

[11] Patent Number: 4,554,365

[45] Date of Patent: Nov. 19, 1985

[54] PROCESS FOR PREPARING OXABICYCLOALKANE COMPOUNDS

[75] Inventor: Albertus J. Mulder, Amsterdam, Netherlands

[73] Assignee: Shell Oil Company, Houston, Tex.

[21] Appl. No.: 635,784

[22] Filed: Jul. 30, 1984

[30] Foreign Application Priority Data

Aug. 12, 1983 [GB] United Kingdom ............... 8321713

[51] Int. Cl.[4] .......................................... C07D 493/08
[52] U.S. Cl. ................................................. 549/463
[58] Field of Search ........................................ 549/463

[56] References Cited

FOREIGN PATENT DOCUMENTS 81893  6/1983  European Pat. Off. .

Primary Examiner—Richard A. Schwartz
Assistant Examiner—Bernard I. Dentz

[57] ABSTRACT

The invention provides a process for preparing a 7-oxabicyclo[2.2.1]heptan-2-ol, which comprises treating a liquid-phase mixture of the corresponding cyclohex-3-en-1-ol, an aldehyde containing at least two carbon atoms and a suitable solvent, with oxygen in the presence of a catalyst which is soluble in the reaction mixture and which comprises a praseodymium compound and at least one compound selected from compounds of molybdenum, niobium, tantalum, tungsten, uranium and vanadium.

15 Claims, No Drawings

PROCESS FOR PREPARING OXABICYCLOALKANE COMPOUNDS

BACKGROUND OF THE INVENTION

1. Field of the Invention

This invention relates to a process for preparing oxabicycloalkane compounds and to the compounds whenever prepared by the process and their use as intermediates in the preparation of herbicidally active oxabicycloalkane compounds 2. Description of the Prior art European Patent Application No. EP-A-81893 discloses a broad class of oxabicycloalkane compounds having herbicidal activity, together with various classes of intermediates and processes whereby the herbicidally active compounds may be prepared.

One subclass of the oxabicycloalkane compounds disclosed in EP-A-81893 comprises oxabicyclo[2.2.1-]heptane compounds which may be represented by the general formula

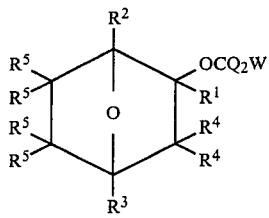

(III)

wherein $R^1$ is a hydrogen atom or $C_{1-6}$ alkyl group optionally substituted by up to 3 fluorine, chlorine and/or bromine atoms; $R^2$ is a hydrogen atom or a $C_{1-6}$ straight-chain alkyl group; $R^3$ is a hydrogen atom; a $C_{1-10}$ alkyl group; a cyano group; an alkyl group substituted by one or more halogen atoms or by a hydroxy group, a cyano group, a $C_{1-6}$ alkoxy group, an aryloxy group, a $C_{1-6}$ alkylsulphonyl group, an arylsulphonyl group, an aralkylsulphonyl group, an azido group, a $C_{1-6}$ alkoxycarbonyl group, an aralkoxy carbonyl group, a hydroxycarbonyl group, a phosphoryl group, a phosphoryloxy group, or an amine oxide, carbamoyl or thiocarbamoyl group in which each nitrogen is substituted by hydrogen or by 1 or 2 $C_{1-4}$ alkyl groups; a $C_{2-4}$ alkenyl or alkynyl group; an aryl or aralkyl group, each containing from 6 to 11 carbon atoms including 1 to 4 carbon atoms in the alkyl portion and optionally ring substituted by one or more fluorine, chlorine and/or bromine atoms or by a $C_{1-2}$ alkyl or alkoxy group, each optionally substituted by one or more fluorine and/or chlorine atoms; a group —CSNH$_2$; a group —CO$_2$R$^6$ or —CON(R$^6$)$_2$ in which R$^6$ is a hydrogen atom or a $C_{1-6}$ alkyl group; or a $C_{1-6}$ acyl group or an oxime or an acetal derivative of said acyl group; each $R^4$ is independently a hydrogen atom; an alkyl group optionally substituted by up to 3 halogen atoms; a hydroxy group; or a $C_{1-4}$ alkoxy group; each $R^5$ independently is a hydrogen atom, a $C_{1-4}$ alkyl group optionally substituted by up to 3 halogen atoms, or a chlorine or bromine atom; both of Q are hydrogen atoms or flurine atoms; and W is an optionally-substituted unsaturated group of up to 4 carbon atoms; an optionally substituted aryl or heterocyclic group containing up to 14 carbon atoms; a $C_{3-10}$ cycloaliphatic group optionally substituted by $C_{1-3}$ alkyl; or a $C_{3-10}$ secondary alkyl group.

EP-A-81893 describes the preparation of the compounds of formula III by a process which comprises reacting an oxabicycloalkane compound (a 7-oxabicyclo[2.2.1]heptan-2-ol) of formula

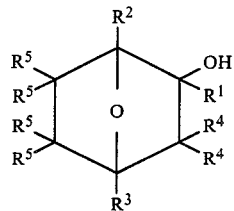

(I)

wherein $R^1$, $R^2$, $R^3$, $R^4$ and $R^5$ are as defined above, with a compound of formula WCQ$_2$L wherein W and Q are as defined above and L represents a leaving group, for example a halogen atom, especially a bromine, chlorine or iodine atom, or an organic sulphonyloxy group, for example a mesyloxy or tosyloxy group.

The reaction is preferably carried out in the presence of a strong base, for example an alkali metal hydride, hydroxide or carbonate, for example sodium hydride, sodium hydroxide or potassium carbonate. Preferably an inert solvent is used; typical solvents include ethers, sulphoxides, aromatic hydrocarbons and chlorinated hydrocarbons, for example diethyl ether, tetrahydrofuran, dimethyl sulphoxide, toluene and methylene chloride. It may be desired to include a catalyst for the reaction; suitable catalysts include organic bases, such as tertiary amines and quaternary ammonium compounds, for example triethylamine or tetrabutylammonium iodide. Suitable temperatures for the reaction are, for example from 0° to 120° C., preferably from 20° to 100° C.

The compounds of formula I are prepared by epoxidation-cyclisation of the corresponding unsaturated cyclic alcohol, i.e. a cyclohex-3-en-1-ol compound of formula

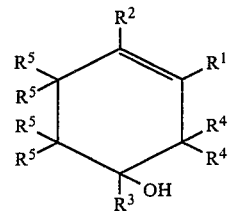

(II)

wherein $R^1$, $R^2$, $R^3$, $R^4$ and $R^5$ are as defined above.

The epoxidation is effected by action of a peroxide, such as m-chloroperbenzoic acid, peracetic acid, tert-butyl hydroperoxide (TBHP) or equivalent peroxide reagents. Preferably, an oxidation with TBHP is conducted in the presence of an appropriate transition metal catalyst. Suitable transition metal catalysts are complexes of metals of atomic numbers 22–31, 40–49 and 72–81. Preferably, the complex is an organic complex, for example with beta-diketones, o-hydroxybenzaldehydes or o-hydroxybenzophenones and particularly with acetylacetone. While any of these transition metal catalysts can be used, those of vanadium or molybdenum are preferred; for example, vanadium (IV) bis(2,4-pentanedionate)oxide is preferred. The reaction is suitably conducted in the presence of an inert solvent such as a chlorinated hydrocarbon, ether or hydrocarbon.

The resulting product epoxy-alcohol may be purified or may be cyclised without isolation.

The cyclisation step is carried out, particularly when the peroxide used to effect epoxidation is non-acidic, by treating the epoxy-alcohol with an acid, preferably a relatively strong acid such as sulphuric or a sulpnonic acid, such as methanesulphonic acid, benzenesulphonic acid or, especially, p-toluenesulphonic acid. The reaction is suitably carried out in a solvent of the type previously described for use in the preparation of the epoxy-alcohol.

The compounds of formula II are either known materials from natural sources or may be synthesised as described in EP-A-81893.

The present invention provides a readily effected single-step process for the preparation of oxabicycloalkane compounds of formula I which avoids the necessity for peroxide reagents.

SUMMARY OF THE INVENTION

According to the present invention there is provided a process for preparing an oxabicycloalkane compound of formula I as defined above which process comprises treating a liquid-phase mixture of a compound of formula II as defined above, an aldehyde containing at least two carbon atoms and a suitable solvent, with oxygen in the presence of a catalyst which is soluble in the reaction mixture and which comprises a praseodymium compound and at least one compound selected from compounds of molybdenum, niobium, tantalum, tungsten, uranium and vanadium.

In connection with the moieties $R^1$, $R^2$, $R^3$, $R^4$, $R^5$ and W, unless otherwise specifically stated herein, an aliphatic group preferably has up to 6, especially up to 4, carbon atoms, and an aryl group is preferably a phenyl group. Preferred halogen atoms are fluorine, chlorine and bromine atoms.

$R^1$ is preferably a methyl group or, especially, a hydrogen atom.

$R^2$ is preferably a hydrogen atom or a $C_{1-3}$ straight-chain alkyl group. Advantageously $R^2$ is a methyl or ethyl group, more preferably a methyl group.

$R^3$ is preferably a hydrogen atom; a $C_{1-6}$ alkyl group optionally substituted by up to 3 fluorine, chlorine and/or bromine atoms or by a hydroxy, cyano, $C_{1-6}$ alkoxy, $C_{1-6}$ alkylsulphonyl, phenylsulphonyl or benzylsulphonyl group; a $C_{2-4}$ alkenyl or alkynyl group; or an aryl or aralkyl group containing 6 to 11 carbon atoms and 1 or 2 carbon atoms in any alkyl portion, optionally ring substituted by one or more fluorine, chlorine and/or bromine atoms or by a $C_{1-2}$ alkyl or alkoxy group optionally substituted by one or more fluorine and/or chlorine atoms.

More preferably $R^3$ is a hydrogen atom, a $C_{1-4}$ alkyl group optionally substituted by a halogen atom, a hydroxy group, a cyano group, a $C_{1-3}$ alkoxy group, a methylsulphonyl group or a phenyl sulphonyl group, or $R^3$ is an allyl group, a phenyl group or a benzyl group.

Most preferably $R^3$ represents a hydrogen atom or a $C_{1-3}$ alkyl group optionally substituted by one or more halogen atoms. Especially preferred group $R^3$ are methyl, ethyl, isopropyl and 1-chloro-1-methylethyl groups. $R^3$ is most preferably an isopropyl group. Each $R^4$ and $R^5$ preferably independently represents a hydrogen atom or a methyl or ethyl group, most preferably a hydrogen atom.

The compound of formula II wherein $R^1$, $R^4$ and $R^5$ are all hydrogen atoms, $R^2$ is a methyl group and $R^3$ is an isopropyl group is 4-terpeneol.

The aldehyde employed in the process of the invention may be an aliphatic aldehyde, e.g. an aliphatic aldehyde containing 2 to 6 carbon atoms, or an aromatic aldehyde, e.g. benzaldehyde. Aliphatic aldehydes containing 2 to 4 carbon atoms are preferred. Propionaldehyde has been found to be very suitable. During the course of the reaction, the aldehyde is co-oxidised to the corresponding acid, e.g. propionaldehyde is oxidised to propionic acid.

The aldehyde is preferably used in an amount of at least 1 mol per mol of olefinically-unsaturated compound. Preferably the amount of aldehyde is in the range 1 to 3 mol per mol of olefinically-unsaturated compound. Amounts of aldehyde in the range 1.1 to 2 mol per mol olefinically-unsaturated compound have been found to give very good results.

The solvent may be any suitable solvent which is substantially inert to oxidation under the reaction conditions employed and which gives rise to a homogeneous reaction mixture. The solvent may be a single solvent or a mixture of solvents, and may conveniently be an ester, a ketone or a carboxylic acid. Advantageously the solvent comprises at least one solvent selected from $C_{1-6}$ alkyl esters of $C_{2-6}$ carboxylic acids, $C_{3-6}$ ketones and $C_{2-6}$ carboxylic acids, and more preferably the solvent comprises at least one solvent selected from methyl and ethyl esters of acetic and propionic acids, acetone, methyl ethyl ketone, acetic acid and propionic acid.

The process of the invention may be effected over a wide range of temperatures. Temperatures in the range from 30° C. to the reflux temperature of the reaction mixture are very suitable. Preferred reaction temperatures are in the range 30° to 60° C.

The catalyst is preferably in the form of salts of one or more organic acids and advantageously the catalyst comprises a $C_{2-6}$ carboxylic acid, preferably acetate or propionate, salt of praseodymium, of one or more metals selected from molybdenum, niobium, tantalum, tungsten, uranium and vanadium and optionally of one or more other metals. The praseodymium may conveniently be incorporated in the catalyst in the form of a mixture of praseodymium and other metal salts in the relative proportions in which they are found in nature. Conveniently therefore the catalyst may contain a didymium salt. It is advantageous for the catalyst additionally to contain a cobalt or manganese, preferably a cobalt, salt. Advantageously the catalyst contains an uranium or vanadium salt.

The amount of catalyst to be employed will vary according to the catalyst composition, as will be appreciated by those skilled in the art. However, in general the weight ratio of praseodymium compound to compound selected from compounds of molybdenum, niobium, tantalum, tungsten, uranium, and vanadium may be in the range 10:1 to 1:50, conveniently 5:1 to 1:25. A cobalt or manganese salt may advantageously be incorporated in the catalyst in an amount in the range $4 \times 10^{-5}$ to $6 \times 10^{-3}$ parts, preferably $8 \times 10^{-5}$ to $3 \times 10^{-3}$ parts, per part by weight of praseodymium compound. The overall amount of catalyst employed may conveniently be in the range 0.05% to 8%, preferably 0.1% to 4% based on the weight of the compound of formula II in the liquid-phase mixture.

The invention further comprises oxabicycloalkane compounds of formula I as defined above whenever prepared by the process of the invention, and to their use as intermediates in the preparation of oxabicycloalkane compounds of formula III as defined above by the process which comprises reacting the compound of formula I with a compound of formula $WCQ_2L$, wherein W, Q and L are as defined above.

W is conveniently an alkenyl or alkynyl group containing from 2 to 4 carbon atoms; a 4-pyrimidinyl group; a 2-pyrazinyl group; a 3-pyridazinyl group; a 2-pyridinyl group; a 2-furyl group; or a phenyl group optionally substituted by one or more of halogen, cyano, amino, $C_{1-3}$ alkoxy or alkylthio, each optionally substituted by one or more fluorine and/or chlorine atoms, or $C_{1-2}$ alkyl optionally substituted by one or more fluorine and/or chlorine atoms, hydroxy, $C_{1-2}$ alkoxy, or $C_{1-2}$ alkylthio.

Optional substituents for W include hydroxy; cyano; nitro; fluorine, chlorine, bromine and iodine atoms; alkyl, haloalkyl, alkoxy, haloalkoxy, alkylthio, haloalkylthio, alkylsulphinyl and alkylsulphonyl group; alkenyl or alkynyl of up to 4 carbon atoms; phenyl, phenoxy, benzyl and benzyloxy groups; and aminocarbonyl, carboxyl, amino, aminoalkyl and alkanoylamino groups, in each of which hydrogen can be replaced by $C_{1-4}$ alkyl.

Heterocyclic groups W may be mono- or bi-cyclic, and preferably contain up to 3, especially 1 or 2, oxygen, nitrogen and/or sulphur atoms. The rings may be saturated or unsaturated. Typical heterocyclic groups W include for example imidazolyl, triazolyl, thiadiazolyl, 2-quinolinyl, 1-isoquinolinyl, pyrrolyl, N-methylimidazolyl, N-methylpyrazolyl, isoxazolyl, oxazolyl, isothiazolyl, thiazolyl, thienyl and 5-methyl-2-furyl.

An aryl group W may for example be a naphthyl or, especially, phenyl group.

A cycloaliphatic group W preferably has from 3 to 6 carbon atoms in the ring, and may for example be a cycloalkyl group. Typical cycloaliphatic groups W include for example cyclopropyl, 1-methylcyclopropyl, cyclohexyl and cyclohexenyl groups.

Optionally substituted unsaturated groups W include for example cyano groups and $C_{2-4}$ alkenyl and alkynyl groups, for example ethynyl groups.

For example, W may be a cyano group; a $C_{2-4}$ alkenyl or alkynyl group, a pyrimidinyl group; a pyrazinyl group; a pyridazinyl group; a pyridyl group; a furyl group; a naphthyl group; or a phenyl group optionally substituted by one or more especially 1 to 3, of hydroxy; cyano; halogen; $C_{1-3}$ alkoxy, alkylthio or alkylsulphinyl, each optionally substituted by halogen; benzyloxy; $C_{1-3}$ alkyl optionally substituted by halogen, hydroxy, amino, alkanoylamino, alkoxy or alkylthio; and amino, carboxyl or aminocarbonyl.

Preferably, W is a $C_{2-4}$ alkenyl or alkynyl group; a 4-pyrimidinyl group; a 2-pyrazinyl group; a 3-pyridazinyl group; a 2-pyridyl group; a 2-furyl group; or a phenyl group optionally substituted by one or more of halogen, cyano, amino, $C_{1-3}$ alkoxy or alkylthio each optionally substituted by one or more fluorine and/or chlorine atoms, or $C_{1-2}$ alkyl optionally substituted by one or more fluorine and/or chlorine atoms, or by hydroxy, $C_{1-2}$ alkoxy or $C_{1-2}$ alkylthio.

Most preferably W is an unsubstituted pyridyl, especially a 2-pyridyl, group, or a phenyl group which is unsubstituted or, advantageously, which is substituted by one or two substituents selected from methyl groups, chlorine atoms and fluorine atoms. Such substituents are preferably in the 2- or 2,6-positions. Typical groups W include 2-pyridyl, phenyl, 4-fluorophenyl, 2-chlorophenyl, 2-fluorophenyl, 2-methylphenyl or 2,6-dichloropheny. W may also advantageously represent an ethynyl group.

Preferably each Q is a hydrogen atom.

The invention will be further understood from the following examples thereof which were effected by the following general procedure. In the Examples, unless otherwise indicated parts, ratios and percentages are parts, ratios and percentages by weight and temperatures are in °C.

A solution of 4-terpeneol in the chosen solvent was heated under nitrogen to 48° C. in a reactor equipped with a mantle through which "FREON TF" (trade mark) (1,1,2-trichloro-1,2,2-tricluoroethane, b.p. 48° C.) (also sold as FREON 113") (trade mark) was circulated as heat-exchange medium, by means of which reaction temperature were generally maintained in the range 48° to 53° C. Catalyst was introduced as a solution in propionic acid.

Propionaldehyde was streamed at constant rate into the reaction mixture and the nitrogen was replaced by oxygen. The propionaldehyde was added over the course of 1 to 3 hours, depending on the rate of reaction. The course of the reaction was monitored by hourly withdrawal of a sample which was analysed by gas chromatography, or in some cases by nuclear magnetic resonance or infra-red spectroscopy. Loss of propionaldehyde from the reactor was minimised by means of condensers at 10° C. and −20° C. coupled in series, condensate being returned to the reactor.

Reaction was terminated by replacing the oxygen or air by nitrogen and cooling the reactor to ambient temperature (20° C.). After filtration, the reaction mixture was diluted with pentane, washed with saturated aqueous sodium chloride to remove water-soluble species (mostly propionic acid), and volatiles were removed by vacuum distillation. Products were identified by nuclear magnetic resonance and infrared spectroscopy and using gas-liquid chromatography.

In the examples which follow the didymium acetate used in preparing the catalysts was didymium acetate ex Lindsay Chemicals Division from which water had been removed by drying in vacuo at 100° C. before grinding to a fine powder, having the following metal oxide composition: $La_2O_3$ (41.83%), $CeO_2$ (0.11%), $Pr_6O_{11}$ (17.37%), $Nd_2O_3$ (29.71%), $Sm_2O_3$ (5.03%), $Gd_2O_3$ (3.20%), $Yb_2O_3$ (0.46%) and remainder ($Eu_2O_3$, $Pm_2O_3$, $Tb_2O_3$, $Dy_2O_3$, $Ho_2O_3$, $Er_2O_2$, $Tm_2O_3$, $Lu_2O_3$) (2.29%).

EXAMPLE 1

The above procedure was followed, using Di(propionate)$_3$/VO(propionate)/Co(propionate)$_2$ (1:0.78:7×10$^{-4}$) (20% solution in propionic acid) as catalyst (0.5% based on the weight of starting material) and acetone as solvent (volume ratio solvent: starting material 3:1). The catalyst was prepared in known manner by refluxing didymium acetate, vanadium oxide ($V_2O_3$) and cobalt acetate in propionic acid until the solids were substantially all dissolved and then distilling off propionic acid until no further acetic acid could be detected in the distillate. The final mol ratio propionaldehyde:starting material was 1.1:1, oxygen was bubbled through at a rate of 6/l hour, and reaction time was 3 hours.

More than 96% conversion of the 4-terpeneol starting material was obtained, with selectivity to the desired 1-(±)-2-exo-hydroxy-1-methyl-4-isopropyl-7-oxabicyclo[2.2.1]heptane product of 86% (i.e. 83% yield based on starting material), 6% of the 1,2-epoxide of 4-terpeneol being obtained as by-product.

EXAMPLE 2

The above procedure was followed, using Di(propionate)$_3$/UO$_2$(propionate)$_2$ (1:0.27) (10% solution in propionic acid) as catalyst (0.8% based on the weight of starting material) and acetone as solvent (volume ratio solvent:starting material 3:1). The catalyst was prepared in known manner by refluxing didymium acetate and UO$_2$(OH)$_2$ in propionic acid until the solids were substantially all dissolved, and then distilling off propionic acid until no further acetic acid could be detected in the distillate. The final mol ratio propionaldehyde:starting material was 1.1:1, oxygen was bubbled through at a rate of 6/1 hour, and reaction time was 3.5 hours.

92% conversion of the 4-terpeneol starting material was obtained, with selectivity to the desired 1-(±)-2-exo-hydroxy-1-methyl-4-isopropyl-7-oxabicyclo[2.2.1]heptane product of 85% (i.e. 78% yield based on starting material), 8% of the 1,2-epoxide of 4-terpeneol being obtained as by-product.

EXAMPLE 3

The above procedure was followed, using Di(propionate)$_3$/UO$_2$(propionate)$_2$/Co(propionate)$_2$ (1:0.27:10$^{-5}$) (10% solution in propionic acid) (prepared in similar manner to catalysts of Examples 1 and 2) as catalyst (0.8% based on the weight of starting material) and ethyl acetate as solvent (volume ratio solvent:starting material 3:1). The final mol ratio propionaldehyde:starting material was 1.1:1, oxygen was bubbled through at a rate of 6/1 hour, and reaction time was 5.5 hours.

88% conversion of the 4-terpeneol starting material was obtained, with selectivity to the desired 1-(±)-2-exo-hydroxy-1-methyl-4-isopropyl-7-oxabicyclo[2.2.1]heptane product of 81% (i.e. 71% yield based on starting material), 5% of the 1,2-epoxide of 4-terpeneol being obtained as a by-product.

COMPARATIVE EXAMPLE A

The above procedure was followed, using Di(propionate)$_3$/Co(propionate)$_2$ (100:1) (20% solution in propionic acid) as catalyst (0.6% based on the weight of starting material) and acetone as solvent (volume ratio solvent:starting material 1.5:1). The final mol ratio propionaldehyde:starting material was 1.5:1, oxygen was bubbled through at a rate of 6/1 hour, and reaction time was 4.5 hours.

Although more than 96% conversion of starting material was obtained, the product was the 1,2-epoxide of 4-terpeneol (selectivity 87%). Fractionation of this product in vacuo yielded 1-(±)-2-exo-hydroxy-1-methyl-4-isopropyl-7-oxabicyclo[2.2.1]heptane in 50% yield, the other 50% being lost by polymerisation.

COMPARATIVE EXAMPLE B

To a solution of 22.3 g of 85% m-chloroperbenzoic acid in 150 ml of methylene chloride was added over 40 minutes a solution of 15.4 g of 4-terpeneol in 30 ml methylene chloride at a temperature about 0° C. The reaction mixture was stirred for 20 hours at ambient temperature (20° C.), then cooled to 5° C. A solid was filtered and rinsed with cold methylene chloride. The combined filtrates were washed successively with one-eighth saturated potassium carbonate, saturated sodium sulphite, and then water, dried and Claisen distilled to yield 8.9 g of 1-(±)-2-exo-hydroxy-1-methyl-4-isopropyl-7-oxabicyclo[2.2.1]heptane product (i.e. 52% yield based on starting material).

What is claimed is:

1. A process for preparing an oxabicycloalkane compound of formula

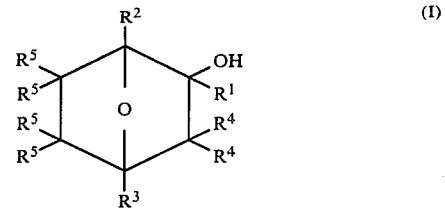

(I)

wherein $R^1$ is a hydrogen atom or $C_{1-6}$ alkyl group optionally substituted by up to 3 fluorine, chlorine and/or bromine atoms; $R^2$ is a hydrogen atom or a $C_{1-6}$ straight-chain alkyl group; $R^3$ is a hydrogen atom; or $C_{1-10}$ alkyl group; a cyano group; an alkyl group substituted by one or more halogen atoms or by a hydroxy group, a cyano group, a $C_{1-6}$ alkoxy group, an aryloxy group, a $C_{1-6}$ alkylsuulphonyl group, an arylsulphonyl group an aralkylsulphonyl group, an azido group, a $C_{1-6}$ alkoxycarbonyl group, an aralkoxy carbonyl group, a hydroxycarbonyl group, a phosphoryl group, a phosphoryloxy group, or an amine oxide, carbamoyl or thiocarbamoyl group in which each nitrogen is substituted by hydrogen or by 1 or 2 $C_{1-4}$ alkyl groups; a $C_{2-4}$ alkenyl or alkynyl group; an aryl or aralkyl group, each containing from 6 to 11 carbon atoms including 1 to 4 carbom atoms in the alkyl portion and optionally ring substituted by one or more fluorine, chlorine and/or bromine atoms or by a $C_{1-2}$ alkyl or alkoxy group, each optionally substituted by one or more fluorine and/or chlorine atoms; a group —CSNH$_2$; a group —CO$_2$R$^6$ or —CON(R$^6$)$_2$ in which R$^6$ is a hydrogen atom or a $C_{1-6}$ alkyl group; or a $C_{1-6}$ acyl group or an oxime or an acetal derivative of said acyl group; each $R^4$ is independently a hydrogen atom; an alkyl group optionally substituted by up to 3 halogen atoms; a hydroxy group; or a $C_{1-4}$ alkoxy group; and each $R^5$ independently is a hydrogen atom, a $C_{1-4}$ alkyl group optionally substituted by up to 3 halogen atoms; or a chlorine or bromine atom; which process comprises treating a liquid-phase mixture of a compound of formula

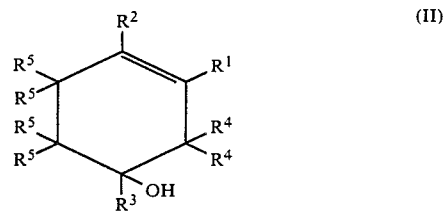

(II)

wherein $R^1$, $R^2$, $R^3$, $R^4$ and $R^5$ are as defined above, an aldehyde containing at least two carbon atoms and a suitable solvent, with oxygen in the presence of a catalyst which is soluble in the reaction mixture and which comprises a praseodymium compound and at least one compound selected from compounds of molybdenum, niobium, tantalum, tungsten, uranium and vanadium.

2. A process according to claim 1, wherein $R^1$ is a hydrogen atom or a methyl group, $R^2$ is a hydrogen atom or a $C_{1-3}$ straight-chain alkyl group, $R^3$ is a hydrogen atom, a $C_{1-4}$ alkyl group optionally substituted by a halogen atom, a hydroxy group, a cyano group, a $C_{1-3}$ alkoxy group, a methylsulphonyl group or a phenyl sulphonyl group, or $R^3$ is an allyl group, a phenyl group or a benzyl group, and each $R^4$ and $R^5$ moiety is independently a hydrogen atom or a methyl or ethyl group.

3. A process according to claim 2, wherein each $R^1$, $R^4$ and $R^5$ moiety is a hydrogen atom, $R^2$ is a methyl group and $R^3$ is an isopropyl group.

4. A process according to claim 1, wherein the aldehyde contains two to four carbon atoms.

5. A process according to claim 4, wherein the aldehyde is propionaldehyde.

6. A process according to claim 1 wherein the solvent comprises at least one solvent selected from $C_{1-6}$ alkyl esters of $C_{2-6}$ carboxylic acids, $C_{3-6}$ ketones and $C_{2-6}$ carboxylic acids.

7. A process according to claim 6, wherein the solvent comprises at least one solvent selected from methyl and ethyl esters of acetic and propionic acids, acetone, methyl ethyl ketone, acetic acid and propionic acid.

8. A process according to claim 1, wherein the catalyst comprises a $C_{2-6}$ carboxylic acid salt of praseodymium, of one or more metals selected from molybdenum, niobium, tantalum, tungsten, uranium and vanadium, and optionally of one or more other metals.

9. A process according to claim 8, wherein the catalyst contains a didymium salt.

10. A process according to claim 8, wherein the catalyst contains a cobalt salt.

11. A process according to claim 8, wherein the catalyst contains a uranium or vanadium salt.

12. A process according to claim 8, wherein the carboxylic acid salt comprises acetate or propionate.

13. A process according to claim 1, wherein the aldehyde is used in an amount in the range 1 to 3 mol per mol of the compound of formula II.

14. A process according to claim 1, wherein the reaction temperature is in the range from 30° C. to the reflux temperature of the reaction mixture.

15. A process according to claim 8, wherein the reaction temperature is in the range from 30° to 60° C.

* * * * *